(12) United States Patent
Mane et al.

(10) Patent No.: US 11,124,560 B2
(45) Date of Patent: Sep. 21, 2021

(54) STABLE POOLED BREASTMILK ANTIBODIES FOR ORAL DELIVERY

(71) Applicant: LACTIGA, INC., Toronto (CA)

(72) Inventors: Viraj Mane, Toronto (CA); Rikin Mehta, Chester, NJ (US)

(73) Assignee: LACTIGA, INC., Toronto (CA)

( * ) Notice: Subject to any disclaimer, the term of this patent is extended or adjusted under 35 U.S.C. 154(b) by 0 days.

(21) Appl. No.: 16/622,144

(22) PCT Filed: Jun. 12, 2018

(86) PCT No.: PCT/CA2018/050703
§ 371 (c)(1),
(2) Date: Dec. 12, 2019

(87) PCT Pub. No.: WO2018/227285
PCT Pub. Date: Dec. 20, 2018

(65) Prior Publication Data
US 2020/0123232 A1    Apr. 23, 2020

Related U.S. Application Data

(60) Provisional application No. 62/518,631, filed on Jun. 13, 2017.

(51) Int. Cl.
| | | |
|---|---|---|
| *C07K 16/04* | (2006.01) | |
| *A23L 33/17* | (2016.01) | |
| *A61K 9/00* | (2006.01) | |
| *A61K 35/20* | (2006.01) | |
| *A23K 20/142* | (2016.01) | |

(52) U.S. Cl.
CPC ............. *C07K 16/04* (2013.01); *A23L 33/17* (2016.08); *A61K 9/0053* (2013.01); *A61K 35/20* (2013.01); *A23K 20/142* (2016.05); *A23V 2002/00* (2013.01); *C07K 2317/12* (2013.01); *C07K 2317/21* (2013.01); *C07K 2317/94* (2013.01)

(58) Field of Classification Search
None
See application file for complete search history.

(56) References Cited

U.S. PATENT DOCUMENTS

2015/0335738 A1   11/2015   Himmler

FOREIGN PATENT DOCUMENTS

| BR | PI 0404861-0 A | * | 6/2006 | ............. | A61K 35/20 |
| WO | 2013174971 A1 | | 11/2013 | | |

OTHER PUBLICATIONS

Grodzki et al. 'Antibody purification:Ammonium sulfate fractionation or Gel filtration.' C. Oliver and M.C. Jamur (eds.), Immunocytochemical Methods and Protocols, Methods in Molecular Biology, vol. 588, DOI 10.1007/978-1-59745-324-0_3, © Humana Press, 1995, 1999, 2010.*
Ogundele et al. 'Techniques for the storage of human breast milk: implications for anti-microbial functions and safety of stored milk.' Eur. J. Ped. 159:793-797, 2000.*
Salcedo et al. 'Application of industrial treatments to donor human milk: influence of pasteurization treatments, storage temperature, and time on human milk gangliosides.' NPJ Science of Food. 2:5 ; doi:10.1038/s41538-018-0013-9, 2018.*
English translation of BRPI 0404861-0 A, pp. 1-63. (2006).*
El-Loly, M.M., "Bovine Milk Immunoglobulins in Relation to Human Health", International Journal of Dairy Science (2007); 2(3):183-195.
Hurley et al., "Perspectives on Immunoglobulins in Colostrum and Milk", Nutrients (2011); 3:442-474.
Stoliar et al., "Secretory IgA Against Enterotoxins in Breast-Milk", The Lancet, Jun. 12, 1976, pp. 1258-1261.
Smith, Emil L., "The Immune Proteins of Bovine Colostrum and Plasma", J. Biol. Chem (1946); 164:345-358.
CIPO Examiner's Report Application No. 3,037,383 dated Apr. 29, 2019.
CIPO Examiner's Report Application No. 3,037,383 dated Jun. 25, 2019.
CIPO Examiner's Report Application No. 3,037,383 dated Sep. 9, 2019.
PCT International Application No. PCT/CA2018/050703, International Search Report, dated Aug. 24, 2018, 4 pages.
Canadian Application No. 3,037,383, Notice of Allowance, dated Dec. 10, 2019, 1 page.
Afonso et al, "The Production Process and Biological Effects of Intravenous Immunoglobulin", Biomolecules, vol. 6, No. 15, Mar. 9, 2016.
Akazawa-Ogawa et al, "Heat denaturation of the antibody, a multi-domain protein", Biophysical Reviews, vol. 10, pp. 255-258, Dec. 18, 2017.
Wang et al, "Antibody Structure, Instability, and Formulation", Journal of Pharmaceutical Sciences, vol. 96, No. 1, Jun. 4, 2006.

* cited by examiner

*Primary Examiner* — Nora M Rooney
(74) *Attorney, Agent, or Firm* — DLA Piper LLP US

(57) ABSTRACT

Methods are provided for extracting and purifying maternal antibodies from breastmilk, followed by further processing to facilitate oral ingestion. The methods may be used on breastmilk from any mammal, including humans, for consumption by mammals including humans. Antibodies are well-known immune mediators that are naturally found in abundant supply in breastmilk, and they are passed directly to the offspring via breastfeeding. The methods described herein extract antibodies from breastmilk in a manner that preserves the structure and antigen-specificity while enabling the formulation into products that are optimized for delivery to mammals, including humans. The method comprises (1) breastmilk collection, (2) extraction of antibodies, (3) characterization of antibody structure, degradation, and contamination, and (4) formulation into a dietary supplement (food product) for delivery to mammals, especially humans.

21 Claims, 9 Drawing Sheets

| | A | B | C | D | E |
|---|---|---|---|---|---|
| Standard curve | | | | | |
| | Sample [conc EU/ml] of endotoxin | Abs 410nm, replicate A | Abs 410nm, replicate B | avg Abs | corrected for Blank |
| | Blank | 0.22 | 0.175 | 0.198 | |
| | 1 | 0.786 | 0.75 | 0.768 | 0.571 |
| | 0.5 | 0.48 | 0.51 | 0.495 | 0.297 |
| | 0.25 | 0.36 | 0.332 | 0.346 | 0.148 |
| | 0.1 | 0.25 | 0.236 | 0.243 | 0.045 |

| | A | B | C | D | E | F | G | H | I |
|---|---|---|---|---|---|---|---|---|---|
| Tested samples | | | | | | | | | |
| | Sample | Abs 410nm, replicate A | Abs 410nm, replicate B | avg Abs | corrected for Blank | Measured concentration EU/ml | | Final concentration EU/ml | |
| | Milk (1/500) | 0.58 | 0.606 | 0.593 | 0.395 | 0.687 | | 343.32 | |
| | CF (1/250) | 0.282 | 0.2916 | 0.2868 | 0.089 | 0.158 | | 39.43 | |
| | ASP (1/250) | 0.42 | 0.38 | 0.4 | 0.202 | 0.353 | | 88.31 | |
| | Purified (1/250) | 0.46 | 0.42 | 0.44 | 0.242 | 0.422 | | 105.59 | |

Figure 7

| | ELISA plate schematic | |
|---|---|---|
| | 1 | 2 |
| A | breastmilk antibody, 1°, 2°, pNPP substrate | NO breastmilk antibody, 1°, 2°, NO pNPP substrate |
| B | NO breastmilk antibody, 1°, 2°, pNPP substrate | breastmilk antibody, mismatched 1°, 2°, pNPP substrate |
| C | breastmilk antibody, 1°, NO 2°, pNPP substrate | breastmilk antibody, mismatched 1°, NO 2°, pNPP substrate |
| D | breastmilk antibody, 1°, 2°, NO pNPP substrate | breastmilk antibody, mismatched 1°, 2°, NO pNPP substrate |
| E | empty | empty |
| F | empty | empty |
| G | empty | empty |
| H | empty | empty |

| | Study 1 | |
|---|---|---|
| | 1 | 2 |
| A | 3.883 | 2.065 |
| B | 0.203 | 3.118 |
| C | 0.071 | 0.073 |
| D | 0.046 | 0.047 |
| E | 0.054 | 0.068 |
| F | 0.077 | 0.053 |
| G | 0.056 | 0.051 |
| H | 0.051 | 0.051 |

| | Study 2 | |
|---|---|---|
| | 1 | 2 |
| A | 2.202 | 0.112 |
| B | 0.351 | 0.675 |
| C | 0.074 | 0.086 |
| D | 2.144 | 0.713 |
| E | 0.054 | 0.052 |
| F | 0.056 | 0.054 |
| G | 0.053 | 0.050 |
| H | 0.051 | 0.079 |

Figure 8

|   | HUMAN ANTIBODY: STOCK CONCENTRATION ||| HUMAN ANTIBODY: 1/10 DILUTION ||| 7 | 8 |
|---|---|---|---|---|---|---|---|---|
|   | 1 | 2 | 3 | 4 | 5 | 6 | | |
| A | Refrigerated antibody: control for un-aged, stable antibody ||| Refrigerated antibody: control for un-aged, stable antibody ||| No primary antibody: negative control | No secondary antibody: negative control |
| B | Antibody aged at room temperature for 24 hours ||| Antibody aged at room temperature for 24 hours ||| | |
| C | Antibody aged at 65°C for 24 hours: control for degraded antibody ||| Antibody aged at 65°C for 24 hours: control for degraded antibody ||| | |
| D | Antibody aged at room temperature for 7 days ||| Antibody aged at room temperature for 7 days ||| | |
| E | Antibody aged at room temperature for 14 days ||| Antibody aged at room temperature for 14 days ||| | |
| F | blank ||| blank ||| | |
| G | blank ||| blank ||| | |
| H | blank ||| blank ||| | |

Figure 9

|   | HUMAN ANTIBODY: STOCK CONCENTRATION | | | HUMAN ANTIBODY: 1/10 DILUTION | | | | |
|---|---|---|---|---|---|---|---|---|
|   | 1 | 2 | 3 | 4 | 5 | 6 | 7 | 8 |
| A | 0.9854 | 1.0779 | 1.3103 | 0.2890 | 0.2135 | 0.2148 | 0.1564 | 0.0819 |
| B | 1.1241 | 1.2742 | 1.2983 | 0.2402 | 0.2648 | 0.2665 | 0.1121 | 0.0849 |
| C | 0.6130 | 0.7794 | 0.6537 | 0.1703 | 0.1685 | 0.2162 | 0.1113 | 0.0832 |
| D | 0.7108 | 0.7590 | 0.8873 | 0.2448 | 0.2087 | 0.2312 | 0.1183 | 0.0852 |
| E | 0.9788 | 0.9538 | 1.0376 | 0.2464 | 0.2374 | 0.2833 | 0.1157 | 0.0836 |
| F | 0.0512 | 0.0513 | 0.0512 | 0.0518 | 0.0498 | 0.0508 | 0.0507 | 0.0498 |
| G | 0.0502 | 0.0520 | 0.0496 | 0.0505 | 0.0492 | 0.0494 | 0.0497 | 0.0500 |
| H | 0.0570 | 0.0509 | 0.0507 | 0.0510 | 0.0522 | 0.0506 | 0.0501 | 0.0496 |

STABLE POOLED BREASTMILK ANTIBODIES FOR ORAL DELIVERY

CROSS REFERENCE TO RELATED APPLICATIONS

This application is a National Stage of PCT/CA2018/050703, filed Jun. 12, 2018, which claims priority to U.S. Application 62/518,631, filed Jun. 13, 2017. All of the foregoing are incorporated by reference in their entireties.

FIELD

The present invention is directed to breastmilk-derived antibody formulations. In particular, the invention is directed to breastmilk-derived antibody formulations with improved stability for oral ingestion.

BACKGROUND

The American Public Health Association (APHA) (American Public Health Association, 2007) has recognized that human milk is the most appropriate food for almost all human infants and is an important preventative health measure. However, social, economic, educational, institutional, and political barriers to breastfeeding mean that human milk is underutilized, so the risk of chronic diseases in both mothers and their offspring continues.

At present, no readily accessible method is known for (a) the collection of human breastmilk samples, (b) the extraction from said samples of one or more of those antibodies known to have beneficial properties for human health, (c) the optional characterization of those derived antibodies, and (d) the reduction of those derived antibodies into a stable delivery system with an appropriate shelf-life to allow for storage and simple, preferably oral, ingestion.

Immunoglobulin extraction and endotoxin characterization have been described for biological samples, such as serum or cell culture supernatant, but these extraction and characterization protocols do not readily apply to breastmilk because of its unique properties. These unique properties include antibody concentration, pH, lipid concentration, viscosity, and sugar content, among others.

There is a need for a method that yields a breastmilk-derived, pooled antibody formulation that can withstand long-term storage and is suitable for oral ingestion. Such a method for purification and storage of an important component of breastmilk may contribute to better access to the benefits of breastmilk for infants, children, and adults, thereby improving public health.

BRIEF DESCRIPTION OF THE FIGURES

In figures that illustrate by way of example only a preferred embodiment,

FIG. 7 is a table showing the assay development, and assay results, to identify reagent conditions suitable to test thermostability of breastmilk-derived antibodies;

FIG. 8 is a table showing the assay schematic for testing thermostability of breastmilk-derived antibodies by comparing different temperature conditions and different lengths of incubation, where each antibody condition was tested in triplicate;

FIG. 9 is a table of the sample absorbance readings (at 405 nm) corresponding to the schematic outlined in FIG. 8;

SUMMARY

Figure 1:
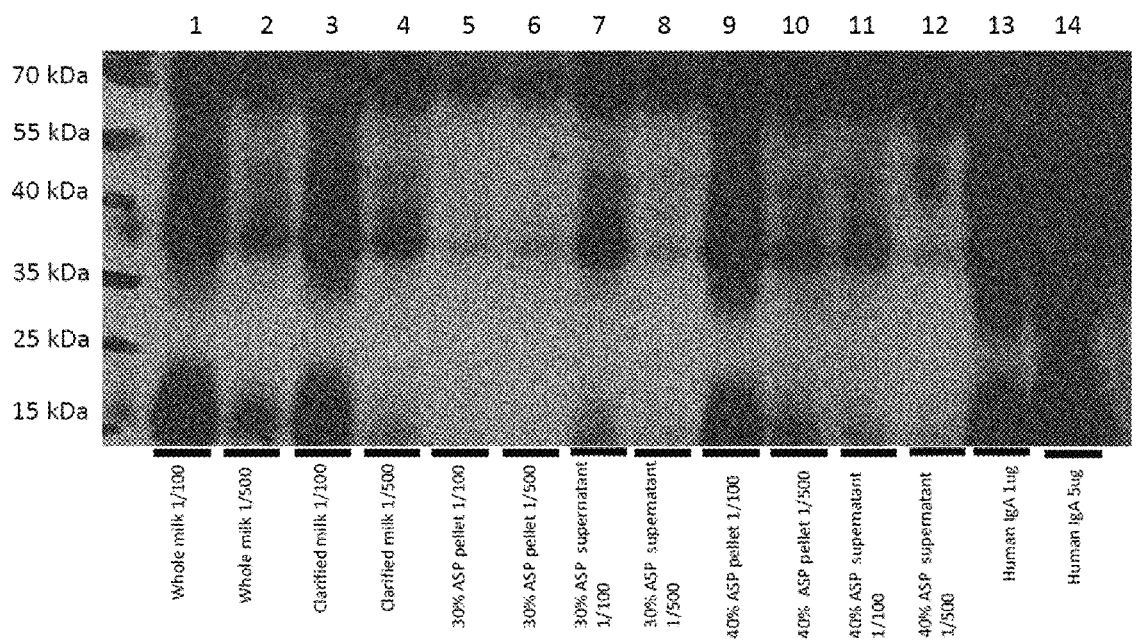
FIG. 1 is a western blot to detect human breastmilk-derived antibodies from whole breastmilk (columns 1-2), clarified milk (columns 3-4), or breastmilk samples that had been precipitated with 30% or 40% ammonium sulfate.

A method of preparing a thermostable antibody composition is provided, comprising the steps of collecting a quantity of milk from a mammalian donor, purifying a non-pasteurized sample of the quantity of milk to extract an antibody fraction, characterizing the antibody fraction to determine the type of antibodies present, and providing a pooled composition of antibodies for use in the preparation of an oral dosage form.

Further provided is a method of preparing a thermostable antibody composition, as above, wherein the thermostable antibody composition is stable for at least two weeks at room temperature.

Further provided is a method of preparing a thermostable antibody composition, as above, wherein the antibody fraction is further characterized to determine the amount of antibodies present.

Further provided is a method of preparing a thermostable antibody composition, as above, wherein the mammalian donor is a human.

Further provided is a method of preparing a thermostable antibody composition, as above, wherein the antibody fraction is non-specific.

Further provided is a method of preparing a thermostable antibody composition, as above, wherein the non-pasteurized sample is purified using ammonium sulfate precipitation.

Further provided is a method of preparing a thermostable antibody composition, as above, wherein the non-pasteurized sample is purified using ammonium sulfate precipitation with an ammonium sulfate concentration of approximately 45% to 65%.

Further provided is a method of preparing a thermostable antibody composition, as above, wherein the non-pasteurized sample is purified using ammonium sulfate precipitation with an ammonium sulfate concentration of approximately 65%.

Further provided is a method of preparing a thermostable antibody composition, as above, wherein the pooled composition of antibodies is at least approximately 90% IgA.

Further provided is a thermostable composition of purified IgA extracted from a quantity of non-pasteurized human breastmilk for use in the preparation of an immune supplement.

Further provided is a thermostable composition of purified IgA extracted from a quantity of non-pasteurized human breastmilk for use in the preparation of an immune supplement, wherein the thermostable composition is stable for at least 24 hours at room temperature.

Further provided is a thermostable composition of purified IgA extracted from a quantity of non-pasteurized human breastmilk for use in the preparation of an immune supplement, wherein the thermostable composition is stable for at least two weeks at room temperature.

Further provided is a thermostable composition of purified IgA extracted from a quantity of non-pasteurized human breastmilk for use in the preparation of an immune supplement, wherein the immune supplement is an oral dosage form.

Further provided is a thermostable composition of purified IgA extracted from a quantity of non-pasteurized human breastmilk for use in the preparation of an immune supplement, wherein ammonium sulfate precipitation at an ammonium sulfate concentration of approximately 45 to 65% is used for the purposes of non-specific fractionation of antibodies and endotoxin reduction.

Further provided is a thermostable composition of purified IgA extracted from a quantity of non-pasteurized human breastmilk for use in the preparation of an immune supplement, wherein the ammonium sulfate concentration is approximately 65%.

Further provided is a thermostable composition of purified IgA extracted from a quantity of non-pasteurized human breastmilk for use in the preparation of an immune supplement, wherein the endotoxin reduction is at least 69% relative to the quantity of non-pasteurized human breastmilk.

Further provided is an immune supplement oral dosage form made using the thermostable composition as above.

Further provided is an immune supplement oral dosage form made according to the method, as above.

The use of ammonium sulfate precipitation is further provided, with an ammonium sulfate concentration of approximately 45 to 65% to prepare a thermostable composition of purified IgA extracted from a quantity of non-pasteurized human breastmilk for use in the preparation of an immune supplement.

Further provided is the use of ammonium sulfate precipitation with an ammonium sulfate concentration of approximately 65% to prepare a thermostable composition of purified IgA extracted from a quantity of non-pasteurized human breastmilk for use in the preparation of an immune supplement.

DETAILED DESCRIPTION

Described herein are processes for the novel stabilization of breastmilk antibodies with thermostable properties. Also described herein is a novel geographical categorization by which maximum benefits may occur when recipients are located within a similar region as the breastmilk donors. Through such geographical characterization of breastmilk, recipients may benefit from antibody supplements when those antibodies are reactive against pathogens to which the recipient is likely to be exposed, and this likelihood is highest when the recipient is in close proximity geographically to the antibody donor(s) and is therefore likely to be exposed to the same pathogens. Factors such as elevation, geographic features, humidity, among others, can affect the spread of pathogens, therefore people who live or work close to each other are more likely to encounter the same pathogen as compared to people who live or work far apart.

Described herein are various steps that, when combined, constitute a novel method to extract, purify, and stabilize maternal antibodies from breastmilk. Various properties of breastmilk (including but not limited to viscosity, antibody composition, antibody concentration, and antibody titer) differ from serum or hybridoma supernatant, therefore processes specific to maternal antibody capture have been previously unknown in the art, and are distinct from existing methods of (non-maternal) antibody capture.

In the preferred embodiment, immunoglobulin extraction from milk involves (1) the milk clarification step described in the examples herein, and (2) the use of 65% ammonium sulfate for precipitation, both of which are distinct from known serum or hybridoma-associated techniques.

The preferred embodiments of the formulations described herein provide for long-term storage of antibodies (ideally at room temperature) which is an ongoing challenge in the development of antibody preparations. For example, in 2014 there was only one orally formulated peptide approved by the US Food and Drug Administration (FDA), highlighting the difficulty faced by the pharmaceutical community in delivering an oral protein therapy that resists degradation.

The formulations and processes of the preferred embodiments described herein provide improved stability for the IgA subtype antibody, for example, and package this antibody to provide beneficial thermostability and easy transport, extending the benefit of breastmilk immunity with respect to larger geographic distribution and minimization/elimination of the spoilage that would occur with milk products.

The processes described herein combine biochemical and analytical techniques to extract naturally-occurring maternal antibodies from the breastmilk of mammals, including humans. While the formulations and processes described herein are specific to human antibodies formulated for human consumption, the concept may be applied to other mammals that produce milk. For example, the formulations and processes described herein may be provided to deliver cow antibodies formulated for cows or sheep antibodies formulated for sheep.

Further, just as a human recipient may benefit from human antibodies (because they will protect against pathogens that are known to infect humans), there may be a benefit to consuming antibodies from a different species. For example, some bovine immunoglobulin products have been designed for human consumption, as in the serum-derived bovine immunoglobulin used to manage enteropathy in human patients in people whose ability to digest is impaired.

Sample Collection

In one embodiment of the present invention, the process of extraction of maternal antibodies begins with the collection of breastmilk from a mammalian donor. Breastmilk may be expressed from the breast by using physical stimulation, a mechanical pump apparatus, a combination of these, or any other method that stimulates the flow of breastmilk from the milk duct. In this embodiment, the preferred workflow may be: (1) collect the sample, (2) transport the sample via refrigeration, (3) process the milk into the formulation of the invention soon after collection. In situations where sample processing cannot occur rapidly (i.e. on the same day), samples may be refrigerated (during transport), then frozen until ready for processing. Alternatively, the sample may also be directly frozen shortly after acquisition. The overall goal is to minimize the time that whole breastmilk sits at or near ambient room temperature. Preferably, freeze/thaw cycles of the breastmilk are avoided as these may damage the structure of the antibodies in the breastmilk.

To promote the sterile collection of breastmilk, the breast and nipple will be treated with an alcohol wipe or other cleanser. Cleaners, including alcohol wipes or soaps, that are already in use to sterilize/disinfect human skin surfaces are suitable for this purpose. However, strong acids and bases should be avoided as they may affect the pH and/or acidity of the collected breastmilk sample prior to sample processing.

Similarly, the pump apparatus used to promote the flow of breastmilk should be wiped with cleanser or sterilized with common disinfection techniques before being applied to the breast.

In this embodiment, breastmilk may be collected into suitable bags or containers. The bags or containers may be made of materials such as (but not limited to) plastic, metal, polymer, or combinations thereof, and are preferably selected based on tolerance to various temperatures and lack of cross-reactivity with antibodies. For example, commercial breastmilk storage bags are typically flexible for easy storage, have double zipper seals to prevent leakage, and are stable at various temperatures including room temperature (around 25° C.), refrigeration (around 4° C.), and freezing temperature (below or around −18° C.).

To maximize the stability of antibodies and minimize antibody degradation, freezing temperature is the preferred condition for storage of breastmilk beyond a few days. However, storage of breastmilk under other conditions (such as refrigeration or room temperature) may still compatible with the antibody extraction method, especially if the storage time spent under refrigeration or room temperature is limited.

Unlike with other milk-processing protocols, it is important for the processes of the invention to forgo pasteurization. The pasteurization heat-treatment process would denature/degrade antibodies, which is incompatible with the antibody preservation and stabilization strategy described herein.

Antibody Extraction (Purification)

Antibody extraction or purification methods may range from crude (nonspecific) to highly specific. As used herein, "crude" refers to a method that does not distinguish among antibody subtypes, and retains multiple (or all) antibody subtypes; while "specific" can refer to class-specific or antigen-specific affinity, as described below.

In the preferred embodiment, the general goals of the extraction step are: (1) capture the component of interest, such as antibodies, and preferably all breastmilk antibody subtypes; (2) wash away all other unwanted components, such as water, fats, sugars, proteins, small molecules, and any pathogens or other environmental compounds that may be contaminating the sample; (3) elute (collect) the purified antibody fraction. The preferred method of the invention is designed to capture the broadest possible spectrum of antibodies. Therefore, the preference is for nonspecific methods that facilitate maximum antibody capture. Preferably, all antibodies may be collected from each breastmilk sample to maximize protection against pathogens and to maximize the total antibody recovery. Therefore, crude, pan-antibody purification methods are preferred for the purposes of the invention versus a more restrictive class-specific affinity purification method.

The following are extraction methods that may be used to capture antibodies from breastmilk:

Physicochemical fractionation refers to physical methods, chemical methods, electrical methods, or combinations thereof, for separating certain components (such as antibodies) out of a sample. It may refer to precipitation of antibodies (for example ammonium sulfate precipitation), size exclusion (for example dialysis membranes, size-exclusion resins, and diafiltration devices with high molecular weight cut-off), solid-phase binding (for example immobilized metal chelate chromatography), or separation by electrical charge (for example ion exchange chromatography). Preferably ammonium sulfate precipitation, dialysis purification, and immunoglobulin column-binding purification are used.

Class-specific affinity purification may refer to solid-phase binding and/or biological ligands (for example jacalin, Protein A, Protein G, and Protein L) that capture all antibodies of a particular target class. The five primary immunoglobulin classes are IgA, IgD, IgE, IgG, and IgM, which are distinguished by their heavy chain.

Antigen-specific affinity purification may refer to extraction of antibodies that only bind a particular antigen (without regard to antibody class or isotype). For example, the antigen of interest may be immobilized onto a solid support surface, a resin, or onto beads that enable purification and elution of corresponding antigen-specific antibodies.

Negative selection refers to the removal of unwanted components of breastmilk (for example albumin and casein). It may be desirable to remove certain components because (1) they may not contribute any beneficial nutritional and/or immune effect, and/or (2) their presence may complicate efforts to stabilize and/or formulate the purified breastmilk antibodies of interest.

Antibody Characterization

The following methods may be used to characterize antibodies derived from breastmilk. Each of these methods yields unique information about the structure or purity of the antibody sample. They may be used to ensure that the collected antibodies satisfy requirements for integrity (degradation) and contamination.

Mass spectrometry (MS) may be used for biophysical characterization of antibody preparations at the protein, peptide, and amino acid residue levels. This tool may be used to assess higher order structure, aggregation, and antibody complexation. For example, MS may be used to gauge whether antibodies are intact or have degraded into smaller peptides or amino acids.

Determination of yield and titer: the related terms yield and titer have important differences. The yield refers to the total antibody quantity in the final preparation, calculated as the antibody concentration multiplied by the volume; antibody concentration may be derived from optical measurements. However, concentration and yield do not account for the functional activity of the antibody molecules in this preparation. Functional activity, or titer, is a functional concentration or dilution-factor of an antibody solution against a particular antigen. An ELISA immunoassay-based dilution series is a common method by which titer may be determined.

Assessment and containment of contamination: biologically-derived extracts such as antibodies are often tested for contamination by microbes including (but not limited to) viruses, fungi, parasites, bacteria, and bacterial lipopolysaccharide (LPS), also known as endotoxin. Assays that demonstrate an endotoxin-decontamination benefit of the antibody purification protocol are preferred. The commercial-grade antibody purification protocol will follow current good manufacturing practice (CGMP) requirements, which serve as preventive measures and precautions to help protect product and prevent contamination. Beyond the protections afforded by CGMP practices, purification kits may also be used to, for example, remove LPS from the biologically-derived extracts described herein.

X-ray crystallography: crystallography is a technique by which the 3-dimensional structure of a molecule can be assessed, and has been used historically to derive the structure of antibodies. It may be used to determine whether purified antibodies have retained their typical Y-shaped structure after the aforementioned purification steps.

Antibody Formulation and Route of Administration

In many jurisdictions, oral ingestion (whether liquid, tablet, etc.) is a regulatory requirement for a product to be classified as a dietary supplement. Oral ingestion is therefore the preferred product delivery system for dietary supplements according to the present embodiments, in addition to user convenience and, subsequently, user compliance. IgA-rich breastmilk consumption is a straightforward way to obtain maternal antibodies, however (1) milk spoils over time, (2) adults may be uncomfortable drinking breastmilk, and (3) breastmilk donors may unwittingly pass on contaminants or pathogens due to nonsterile milk handling or due to abundance of pathogens in the milk itself.

Breastmilk-derived antibodies may be formulated to maximize their solubility in the intended diluent, which may be (for example) milk. Antibody formulation may also be designed to maximize the stability of antibodies in the gastrointestinal tract, which is known to differ in pH across the stomach, small intestines, and large intestines, and may be modified for different recipients such as human or non-human infants, children, adolescents, and adults. For example, children may prefer gummy form while adults may prefer powders or caplets. These formulations, and others, are described below. Furthermore, the formulation may be designed to promote subsequent uptake of antibodies by the gastrointestinal tissue of the recipient. For example, the antibody formulation may be ingested along with a dose of e.g. sodium bicarbonate (baking soda) to temporarily and safely alter the pH and/or protease activity of the gut environment to promote the activity and stability of the antibodies.

The described product should be Generally Recognized As Safe (GRAS) because (1) antibodies are a naturally-occurring component of breastmilk, (2) breastmilk is safe for consumption, and (3) no exogenous or synthetic components are being added. The following may be appropriate oral product formulations for antibodies derived from breastmilk according to the preferred embodiments, and each has particular advantages:

Tablet: these are available in many different shapes and sizes, are stable for a long time, and are simple to make: One or more active ingredients are combined with so-called excipients (carrier substances that help hold the tablet together) and then pressed into tablet form. Tablets may be coated or uncoated. Coatings may prevent dampness, block bacterial contamination, facilitate easier swallowing, and/or may protect against gastric acid.

i. Fizzy tablets: Fizzy (effervescent) tablets are dissolved in a glass of water for drinking. They are well suited for people who have difficulty swallowing, and can have a faster effect than non-fizzy tablets because the medication has already dissolved by the time it arrives in the stomach.

ii. Chewable tablets and lozenges: These contain active ingredients intended to have an effect in the throat, for example for a sore throat, or active ingredients that can be absorbed through the lining of the mouth. These tablets are either chewed or sucked on.

iii. Sublingual tablets (from the Latin words sub, meaning "under", and *lingua*, meaning "tongue"): These tablets dissolve under the tongue, and the active ingredient is absorbed directly through the lining of the mouth.

Capsule, Softgel & Gelcap: Capsules have a shell—usually made of gelatin—and inside the shell is the medication in the form of a powder, granulate or liquid. The shell dissolves in the stomach or bowel and then releases the active ingredient. Capsules are long-lasting and tasteless, and sensitive active ingredients keep well in capsules. Chewable capsules may also facilitate absorption of the active ingredient through the lining of the mouth.

Time-release tablets and capsules: Time-release (sustained-release) tablets and capsules are designed to release their active ingredients more gradually, which can reduce the number of doses needed to cover a given period.

Powder and Granulates, Teas, Drops, & Liquids:

i. Powder and Granulates: Drugs in powder or granulate form are usually dissolved in water to be swallowed. An example is vitamin C powder.

ii. Teas: mixtures of dried plant material that are put into hot water to release the active ingredients. There are also instant teas that contain plant extracts or essential oils.

iii. Drops: either the liquid itself is the active ingredient of the medicine, or the active ingredient has been dissolved in liquid, usually in water or a mixture of water and alcohol. Doses are given in numbers of drops.

iv. Liquids and Syrups: with liquid products, one or more active ingredients are usually dissolved or suspended in water. The liquid itself may also be the active ingredient. These forms are popular for people who have problems swallowing tablets. Concentrated sugar solutions that contain medication are called syrups, and are common for children's products.

EXAMPLES

Ammonium Sulfate and Column Purification

The human breastmilk sample was clarified by centrifugation at 13,000 RPM for 60 minutes to remove all fat from colostrum and milk. After clarification (removal of solid particulates such as lipids and casein), ammonium sulfate precipitation [ASP] (Grodzki & Berenstein, 2009) was used for precipitation of antibodies. A range of 40-45% ammonium sulfate has been described for precipitation of IgG from blood sera (Wingfield, 2001), but a wider range of ammonium sulfate concentrations was used for the purposes of this embodiment to identify the optimal condition for antibodies obtained from breastmilk as opposed to blood sera.

Following ASP, the samples were dialyzed in phosphate buffered saline (PBS) to remove ammonium sulfate and other residues, then further enriched for antibodies with an immunoglobulin [Ig] purification column containing pan-human capture antibodies for IgA, IgG and IgM bound to Sepharose 4B according to common manufacturer protocols (Thermo Fisher Scientific, 2018). Column elution buffer at pH 2.8 (which is the standard for hybridoma-derived antibody elution) was compared against pH 4.0. The pH 2.8 buffer facilitated antibody capture shown by Western Blot (FIGS. 1-2), while pH 4.0 yielded no detectable antibodies in the eluant. To quantify the antibody samples that were detected by Western blot, optimal densitometry [OD] was used to measure protein concentration and obtained readings of 0.1 mg/ml, confirming that the ASP and Ig purification methods described herein yield human antibodies. Upon completion of the purification steps outlined herein, antibody samples were suspended in phosphate buffered saline (PBS), also referred to as "saline" or simply "buffer" by those skilled in the art.

Figure 2:
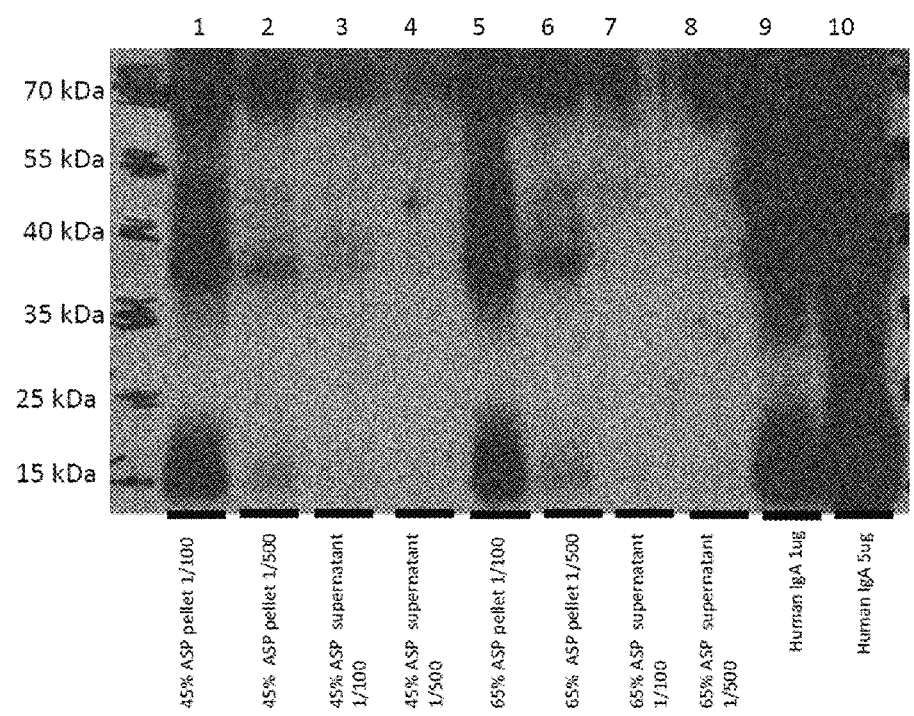
FIG. 2 is a western blot to detect human breastmilk-derived antibodies with the same experimental setup as FIG. 1, but with higher ammonium sulfate concentrations of 45% and 65%.
Figure 3:
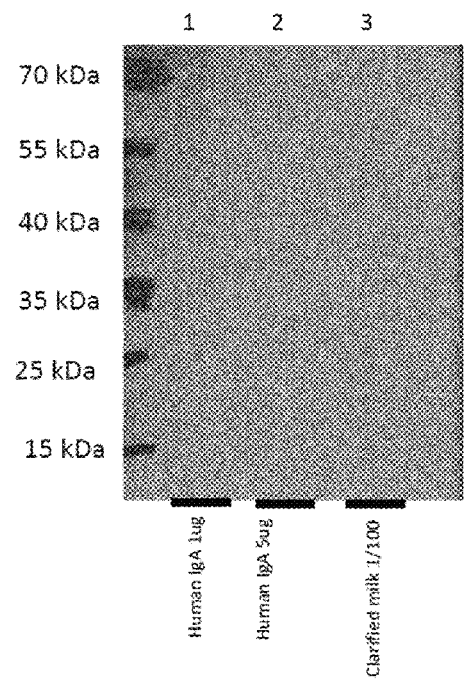
FIG. 3 is a western blot to detect human breastmilk-derived antibodies with a gel as the negative control, in which the primary antibody was eliminated but the secondary antibody was retained.

FIGS. 1-3 show a western blot to detect breastmilk-derived antibodies (10% reducing conditions; 10-second image exposure). As shown by FIG. 1, pan-human-immunoglobulin detection antibodies were used to detect human breastmilk-derived antibodies from whole breastmilk (columns 1-2), clarified milk (columns 3-4), or breastmilk samples that had been precipitated with 30% or 40% ammonium sulfate (columns 5-12), at the dilutions indicated along the X-axis. After Ig column purification, samples were assayed by Western blot to identify the concentration at which antibodies were more present in the precipitated pellet (columns 5, 6, 9, 10) than in the supernatant (columns 7, 8, 11, 12). Commercially-sourced human IgA was used as a positive control (columns 13, 14).

FIG. 2 has the same experimental setup as FIG. 1, but with higher ammonium sulfate concentrations of 45% and 65%. While both of these conditions were superior to the concentrations assayed in FIG. 1, 65% ammonium sulfate was the optimal condition at which maximum signal was present in the precipitated pellet (columns 5, 6) and minimal signal was present in the supernatant (columns 7, 8). Commercially-sourced human IgA was used as a positive control (columns 9, 10). Ammonium percentages both above and below the 40-45% range previously described for serum immunoglobulin precipitations were used for the purposes of this example. It was expected that antibody precipitation from a breastmilk sample may vary considerably from antibody precipitation from serum or cell culture supernatant. As breastmilk has characteristic antibody concentration, pH, viscosity, sugar content, level of contaminants, etc., the approach was to empirically determine the optimum ammonium reagent percentage to use for breastmilk. Indeed, the Western blots reported herein (FIGS. 1 & 2) show that the efficiency of ammonium sulfate immunoglobulin precipitation increases consistently from 30 to 40 to 45 to 65% ammonium sulfate. The 65% ammonium percentage is much greater than the standard 40%, and confirms that protocols derived for serum extractions are not as effective for breastmilk extractions.

FIG. 3 shows a gel as the negative control, in which the primary antibody was eliminated but the secondary antibody was retained. The lack of bands on this gel indicates that there is no nonspecific signal; therefore, the signals in the previous gels represent authentic antibody detection.

Endotoxin Decontamination

Figures 4, 5, 6:
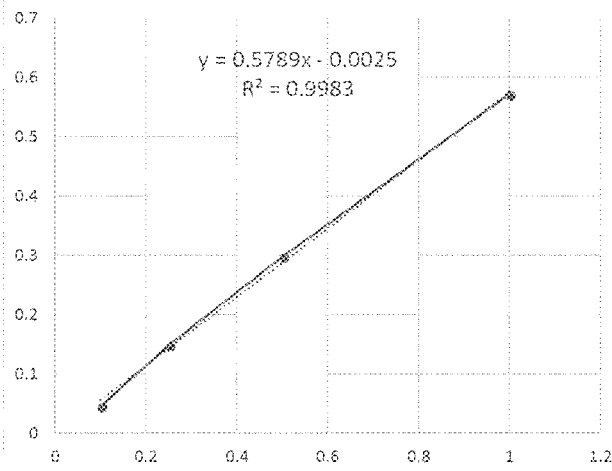
FIG. 4 is a table that shows *E. coli* endotoxin standard samples run on a Limulus Amebocyte Lysate (LAL) Chromogenic Endotoxin Quantitation Kit.
FIG. 5 is a graph showing Standard Curve values calculated in FIG. 4 (column E) with the optical absorbance values (at 410 nm) plotted on the Y-axis and endotoxin concentrations (in EU/ml) plotted on the X-axis.
FIG. 6 is a table showing endotoxin levels measured from each of the sample processing stages (whole breastmilk; clarified milk; ammonium-precipitated Ig; column-purified Ig), where "Ig" is an abbreviation for immunoglobulin and is synonymous with antibody.

The ASP process alters protein solubility, driving aggregation, which helps precipitate out the protein, often referred to as "salting out" proteins from the solution. Given the size, susceptibility to aggregation, solubility, and surface charge of pathogens and other contaminants are different from antibodies, contaminants such as bacteria, viruses, and allergens would not be expected to co-precipitate with the antibody fraction. However, the ASP and Ig purification methods described above yielded an additional and unexpected benefit of sample decontamination in this example. This was unexpected for the collection of polyclonals and given the many different properties between breastmilk and serum or tissue culture supernatants. To exemplify this benefit, endotoxin (a bacterial toxin common in the environment) was measured in this example at each stage of breastmilk processing: total breastmilk, clarified breastmilk, ammonium sulfate precipitated sample, and Ig column-purified sample. As shown in FIGS. 4-6, the sample processing methods led to 69-88% decrease in endotoxin as compared to the initial breastmilk sample. Of note, these experiments were run in standard nonsterile laboratory conditions with relatively high background endotoxin levels. While the laboratory sample results of this example ranged from 39-343 EU/mL of endotoxin, manufacturing-grade GMP clean-room facilities can produce final material with much lower endotoxin, ranging from <0.005 EU/mL to <1.000 EU/mL, suitable for clinical human use.

FIGS. 4-6 show the endotoxin measurement to demonstrate that the antibody purification methods herein also yield decontamination benefits. FIG. 4 shows $E.\ coli$ endotoxin standard samples were run on a Limulus Amebocyte Lysate (LAL) Chromogenic Endotoxin Quantitation Kit. The kit measures endotoxin concentration in a sample by correlating it to a chromogenic signal generated in the presence of endotoxins. Specifically, endotoxins in the sample activate the proteolytic activity of Factor C that is contained in the lysate. The activated Factor C protease then cleaves the kit's chromogenic substrate, resulting in a yellow color that can be quantitated via absorbance at 410 nanometers (nm) and extrapolated against a standard curve.

Four concentrations were used (column A), run in duplicate (columns B, C), then averaged (column D). The corrected values in column E were used to construct the Standard Curve in FIG. 5.

FIG. 5 shows Standard Curve values, calculated in FIG. 4 (column E), in a plot. The optical absorbance values (at 410 nm) are plotted on the Y-axis and the endotoxin concentrations (in EU/ml) are plotted on the X-axis. The R2 value is 0.9983.

FIG. 6 illustrates endotoxin levels measured from each of the sample processing stages of the preferred embodiment (whole breastmilk; clarified milk; ammonium-precipitated Ig; column-purified Ig). As seen in the final column, the processed samples range from 39.43-105.59 EU/ml, a 69-88% reduction from 343.32 EU/ml in non-processed breastmilk.

Antibody Degradation Assay Development

An enzyme-linked immunosorbent assay [ELISA] was developed to measure degradation of breastmilk-derived human antibodies (FIGS. 7 and 8). First, the ELISA plate is coated with purified breastmilk human antibodies, followed by primary (1°) antibodies against the breastmilk human antibodies, followed by enzyme-conjugated secondary (2°) antibodies against the primary antibodies, followed by pNPP substrate whose enzymatic cleavage is detectable by spectrophotometry. The 1° and 2° antibodies are non-human to eliminate unintentional cross-reactivity. The presence of intact breastmilk human antibodies was quantified according to spectrophotometric readouts of absorbance at 405 nm.

FIG. 7 shows the assay development to identify suitable reagent conditions to test thermostability of breastmilk-derived antibodies. As seen in the ELISA plate schematic on the left, A1 was expected to have the highest absorbance signal (at 405 nm) while all other cells are negative controls. In Study 1 (middle panel), A1 has the highest absorbance signal but cells A2 and B2 also have high signals, suggesting that the 2° antibody may be contributing to nonspecific signal. This was addressed by reducing the concentration of 2° antibody in Study 2 (right panel), which did minimize the nonspecific signals in cells A2 and B2. These, and subsequent studies, helped refine the specific conditions to use in the final ELISA assay (see FIG. 8), which determines whether the formulation of the preferred embodiment provides thermostability to the breastmilk human antibody.

FIG. 8 is a schematic to test the stability of breastmilk-derived antibodies under various temperature and time conditions. Non-diluted antibodies were tested in triplicate in Columns 1-3, Rows A-E. A $\frac{1}{10}$ antibody dilution was tested in triplicate in Columns 4-6, Rows A-E. Columns 7 and 8 were used as negative controls lacking primary detection antibody and secondary detection antibody, respectively. Antibodies were incubated under the following conditions: Consistent refrigeration (Row A) representing standard storage antibody storage conditions correlating to minimal antibody degradation; incubation for 24 hours at room temperature, which is typically around 25° C. (Row B); incubation for 24 hours at 65° C. as a control for antibody degradation (Row C); incubation for 7 days at room temperature (Row D); and incubation for 14 days at room temperature (Row E).

In FIG. 9 absorbance readings at 405 nm, taken from each well, are plotted in their respective location on the assay schematic from FIG. 8.

Figure 10:
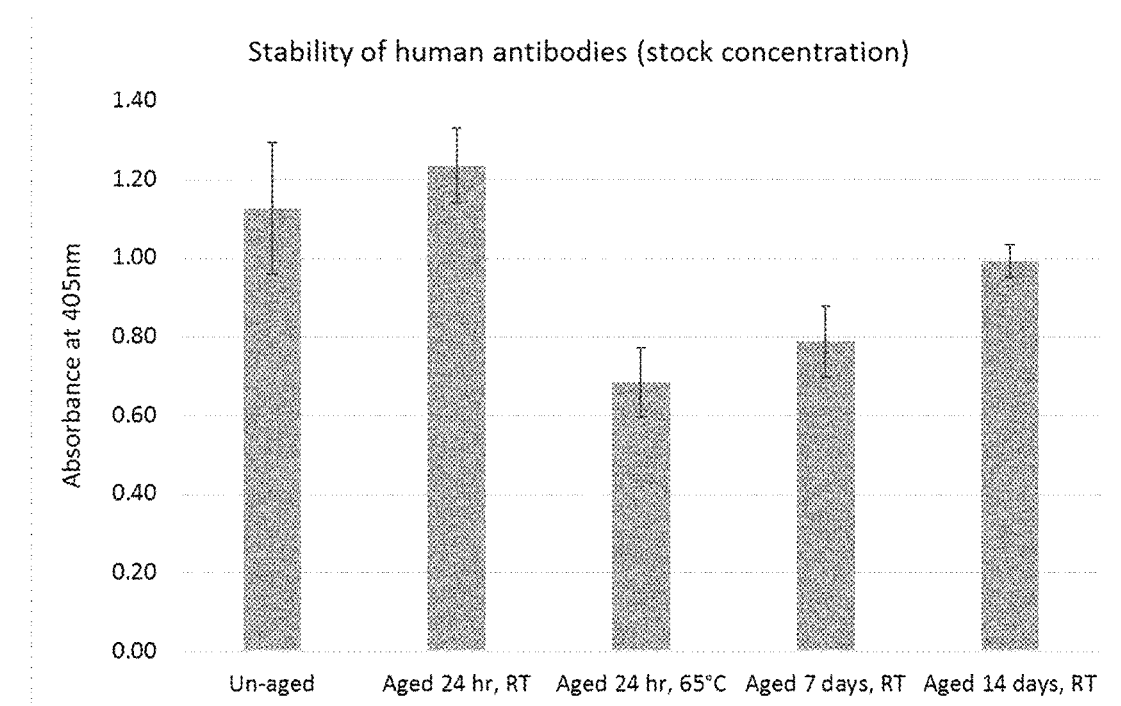
FIG. 10 is a chart with the averages and standard deviation error bars of the absorbance values of the stock antibody samples, corresponding to Columns 1-3 of FIGS. 8 and 9.
Figure 11:
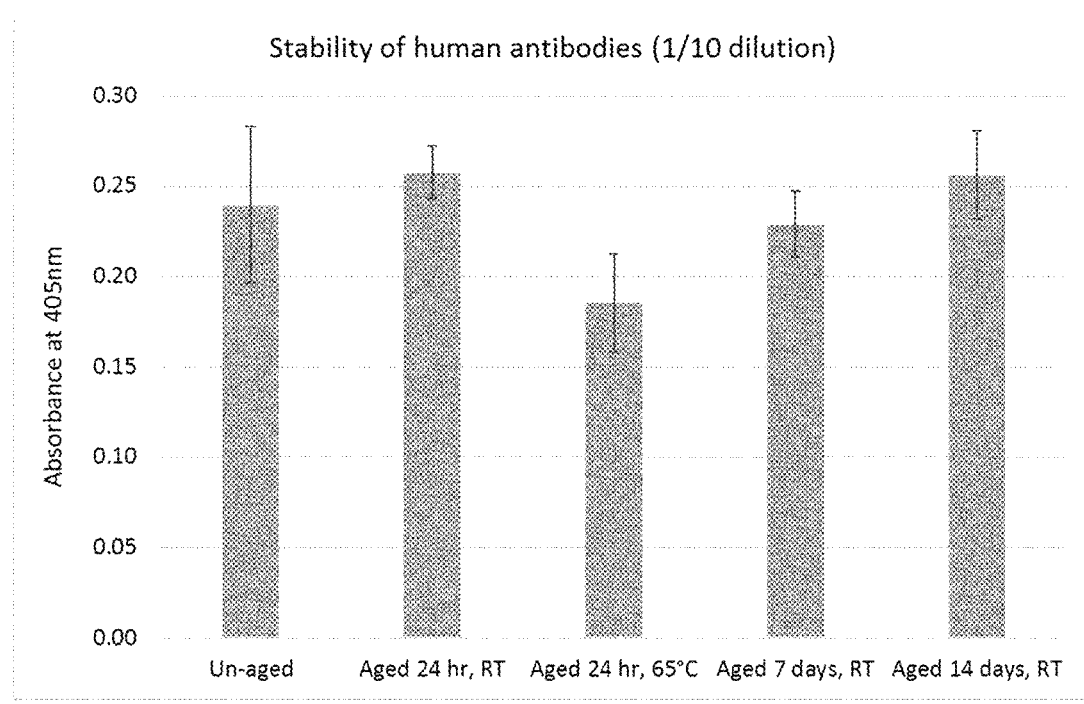
FIG. 11 is a chart with the averages and standard deviation error bars of the absorbance values of the $\frac{1}{10}$-diluted antibody samples, corresponding to Columns 4-6 of FIGS. 8 and 9.

FIGS. 10 and 11 plot the averages and standard deviation error bars of the absorbance values taken from FIG. 9. FIG. 10 is a plot of data from non-diluted antibodies, corresponding to Columns 1-3 from FIGS. 8 and 9. FIG. 11 is a plot of data from $\frac{1}{10}$-diluted antibodies, corresponding to Columns 4-6 from FIGS. 8 and 9.

For both non-diluted antibodies (FIG. 10) and $\frac{1}{10}$-diluted antibodies (FIG. 11), 24 hours of incubation at room temperature had no adverse effect on antibody stability (compare first two bars within each figure). Conversely, 24 hours of incubation at 65° C. led to a statistically significant decrease (p value <0.05) compared to 24 hours of incubation at room temperature for both non-diluted antibodies and $\frac{1}{10}$-diluted antibodies (compare 2nd and 3rd bars). This decrease is consistent with the antibody degradation that is expected after multiple hours of exposure to high heat, and verifies in FIGS. 10 and 11 that this assay distinguishes between intact antibodies (first bar) and degraded antibodies (3rd bar).

Surprisingly, antibodies incubated for 14 days at room temperature (5th bar) had similar stability as un-aged antibodies (1st bar) and antibodies that had been incubated at room temperature for only 24 hours (2nd bar). Furthermore, stability measurements from samples that were incubated for 14 days at room temperature were significantly greater than the samples that underwent 24 hours of incubation at 65° C. (p value <0.05), verifying that the antibodies produced under the specified methods avoid degradation at room temperature for up to 2 weeks without requiring any thermostabilizers.

Various embodiments of the present invention having been thus described in detail by way of example, it will be apparent to those skilled in the art that variations and modifications may be made without departing from the invention. The invention includes all such variations and modifications as fall within the scope of the appended claims.

We claim:

1. A composition of human antibodies substantially free of non-antibody components, the composition comprising purified human IgA with human-specific immunogenicity derived from a sample of non-pasteurized breastmilk, wherein the composition comprises intact antibodies representing more than 81% of total antibodies, the total antibodies comprising the intact antibodies and degraded antibodies, the composition having stability at 25° C. for at least 14 days.

2. An oral formulation comprising the composition of claim 1, wherein the purified human IgA with human-specific immunogenicity is indicated for human use in a predetermined geographic area and is derived from a sample of non-pasteurized human breastmilk obtained from a donor residing in the predetermined geographic area.

3. The composition of claim 1, wherein the intact antibodies represent at least 88% of the total antibodies.

4. The composition of claim 1, wherein the intact antibodies are non-specific.

5. The composition of claim 1, wherein the composition comprises a pooled composition of antibodies with at least 90% purified human IgA.

6. An oral dosage form made using the composition of 1.

7. A method for preparing an antibody composition, comprising the steps of:
collecting a quantity of non-pasteurized breastmilk from a human donor, purifying a sample of the quantity of non-pasteurized breastmilk to extract an antibody fraction using ammonium sulfate precipitation with an ammonium sulfate concentration of approximately 45% to 65%, passing the sample through an immunoglobulin purification column comprising capture antibodies for IgA, IgG, and IgM,
and providing a pooled composition of antibodies for use in the preparation of an oral dosage form or an oral formulation,
wherein the pooled composition comprises intact antibodies representing more than 81% of total antibodies, and the antibody composition is stable at 25° C. for at least 14 days.

8. The method of claim 7, wherein the quantity of non-pasteurized breastmilk is collected from a human donor in a predetermined geographic area, and wherein the oral dosage form or oral formulation is indicated for use in the predetermined geographic area.

9. The method of claim 7, wherein the antibody fraction is further characterized to determine the amount of antibodies present.

10. The method of claim 7, wherein the antibody fraction is non-specific.

11. The method of claim 7, wherein the sample is purified using ammonium sulfate precipitation with an ammonium sulfate concentration of approximately 65%.

12. The method of claim 7, wherein the pooled composition of antibodies is at least 90% IgA.

13. A composition of human antibodies substantially free of non-antibody components, the composition comprising purified human IgA with human-specific immunogenicity derived from a sample of non-pasteurized breastmilk using an ammonium sulfate precipitation with an ammonium sulfate concentration of approximately 45% to 65%, and an immunoglobulin purification column comprising capture antibodies for IgA, IgG, and IgM, wherein the composition comprises intact antibodies representing more than 81% of total antibodies, the total antibodies comprising the intact antibodies and degraded antibodies, the composition having stability at 25° C. for at least 14 days.

14. An oral dosage formulation comprising the composition of claim 13, wherein the purified human IgA with human-specific immunogenicity is indicated for human use in a predetermined geographic area and the purified human IgA is derived from a sample of non-pasteurized human breastmilk obtained from a donor residing in the predetermined geographic area.

15. The composition of claim 14, wherein the intact antibodies represent at least 88% of the total antibodies.

16. The composition of claim 14, wherein the ammonium sulfate concentration is approximately 65%.

17. The composition of claim 14, wherein endotoxin reduction in the composition is at least 69% relative to the sample immediately prior to chemical purification.

18. The composition of claim 14, wherein the intact antibodies are non-specific.

19. The composition of claim 14, wherein the composition comprises a pooled composition of antibodies with at least 90% IgA.

20. An oral dosage form made using the composition of claim 14.

21. The composition of claim 14, wherein endotoxin reduction in the composition is 69-88% relative to the sample immediately prior to chemical purification.

* * * * *